US011465176B2

(12) United States Patent
Chaggares et al.

(10) Patent No.: US 11,465,176 B2
(45) Date of Patent: *Oct. 11, 2022

(54) DUAL FREQUENCY ULTRASOUND TRANSDUCER INCLUDING AN ULTRAHIGH FREQUENCY TRANSDUCER STACK AND A LOW FREQUENCY ULTRASOUND TRANSDUCER STACK

(71) Applicant: FUJIFILM SONOSITE, INC., Bothell, WA (US)

(72) Inventors: Nicholas Christopher Chaggares, Whitby (CA); Guofeng Pang, Ajax (CA); Desmond Hirson, Thornhill (CA)

(73) Assignee: FUJIFILM SONOSITE, INC., Bothell, WA (US)

( * ) Notice: Subject to any disclaimer, the term of this patent is extended or adjusted under 35 U.S.C. 154(b) by 162 days.

This patent is subject to a terminal disclaimer.

(21) Appl. No.: 16/881,598

(22) Filed: May 22, 2020

(65) Prior Publication Data

US 2020/0282427 A1 Sep. 10, 2020

Related U.S. Application Data

(63) Continuation of application No. 15/476,898, filed on Mar. 31, 2017, now Pat. No. 10,661,309.

(Continued)

(51) Int. Cl.
*B06B 1/00* (2006.01)
*A61B 8/00* (2006.01)
(Continued)

(52) U.S. Cl.
CPC .......... *B06B 1/0614* (2013.01); *A61B 8/4494* (2013.01); *B06B 1/0207* (2013.01);
(Continued)

(58) Field of Classification Search
CPC .......... B06B 1/06; B06B 1/02; B06B 1/0614; B06B 1/0207; B06B 1/0688; A61B 8/00;
(Continued)

(56) References Cited

U.S. PATENT DOCUMENTS

2002/0188200 A1* 12/2002 Mauchamp .............. A61B 8/00
600/459
2003/0055337 A1 3/2003 Lin
(Continued)

FOREIGN PATENT DOCUMENTS

WO WO 2009/088307 A1 7/2009
WO WO-2009088307 A1 * 7/2009 ........... A61B 8/4483

OTHER PUBLICATIONS

U.S. Appl. No. 15/476,898 (US 2017/0282215), filed Mar. 31, 2017 (Oct. 5, 2017).
(Continued)

*Primary Examiner* — Daniel L Murphy
*Assistant Examiner* — Amie M Ndure
(74) *Attorney, Agent, or Firm* — Baker Botts L.L.P.

(57) ABSTRACT

A dual frequency ultrasound transducer includes a high frequency ultrasound array and a low frequency transducer positioned behind or proximal to the high frequency ultrasound array. In one embodiment, a dampening material is positioned between a rear surface of the high frequency array and the a front surface of the low frequency array. The dampening preferably is high absorbing of signals at the frequency of the high frequency array but passes signals at the frequency of the low frequency transducer with little attenuation. In additional, or alternatively, the low frequency can angled with respect to the plane of the high frequency transducer to reduce inter-stack multipath reflections. Beamforming delays compensate for the differences in physical (Continued)

distances between the elements of the low frequency transducer and the plane of the high frequency transducer.

15 Claims, 5 Drawing Sheets

Related U.S. Application Data (60) Provisional application No. 62/317,326, filed on Apr. 1, 2016.

(51) Int. Cl.
| | |
|---|---|
| *G10K 11/162* | (2006.01) |
| *G10K 11/30* | (2006.01) |
| *G10K 11/34* | (2006.01) |
| *G10K 11/00* | (2006.01) |
| *G10K 11/02* | (2006.01) |
| *G01S 15/00* | (2020.01) |
| *B06B 1/06* | (2006.01) |
| *B06B 1/02* | (2006.01) |
| *G01S 15/89* | (2006.01) |
| *G10K 11/35* | (2006.01) |

(52) U.S. Cl.
CPC .......... *G01S 15/8952* (2013.01); *G10K 11/02* (2013.01); *G10K 11/162* (2013.01); *G10K 11/30* (2013.01); *G10K 11/346* (2013.01); *G10K 11/355* (2013.01); *B06B 1/0688* (2013.01)

(58) Field of Classification Search
CPC ........ A61B 8/4494; A61B 2017/00969; A61B 17/322; G10K 11/162; G10K 11/30; G10K 11/34; G10K 11/346; G10K 11/355; G10K 11/02; G01S 15/8952; G01S 15/8915; A61F 2/10; Y02P 60/85; F25C 1/12; F25C 2400/14; F25D 2323/122; F25B 40/02; F25B 40/04

See application file for complete search history.

(56) References Cited

U.S. PATENT DOCUMENTS

| | | | |
|---|---|---|---|
| 2003/0173870 A1* | 9/2003 | Simon Hsu | B06B 1/0622 310/334 |
| 2005/0277835 A1* | 12/2005 | Angelsen | G01S 7/52095 600/437 |
| 2006/0052699 A1* | 3/2006 | Angelsen | G01S 7/52042 600/437 |
| 2006/0184022 A1 | 8/2006 | Johnson | |
| 2007/0083120 A1* | 4/2007 | Cain | A61M 37/0092 600/439 |
| 2008/0319356 A1* | 12/2008 | Cain | A61M 37/0092 600/300 |
| 2008/0319375 A1* | 12/2008 | Hardy | B82Y 5/00 600/431 |
| 2009/0178483 A1* | 7/2009 | Angelsen | G01S 7/52022 73/597 |
| 2009/0182237 A1* | 7/2009 | Angelsen | B06B 1/064 600/459 |
| 2010/0036244 A1* | 2/2010 | Angelsen | G01S 7/52077 600/438 |
| 2012/0267986 A1 | 10/2012 | Galluzzo et al. | |
| 2014/0150556 A1* | 6/2014 | Angelsen | A61B 8/08 73/596 |
| 2014/0276247 A1* | 9/2014 | Hall | A61N 1/0432 604/20 |

OTHER PUBLICATIONS

U.S. Appl. No. 15/476,898, Apr. 21, 2020 Issue Fee Payment.
U.S. Appl. No. 15/476,898, Jan. 22, 2020 Notice of Allowance.
U.S. Appl. No. 15/476,898, Dec. 9, 2019 Request for Continued Examination (RCE).
U.S. Appl. No. 15/476,898, Nov. 18, 2019 Advisory Action.
U.S. Appl. No. 15/476,898, Oct. 9, 2019 Response after Final Action.
U.S. Appl. No. 15/476,898, Aug. 9, 2019 Final Action.
U.S. Appl. No. 15/476,898, Mar. 26, 2019 Response after Non-Final Action.
U.S. Appl. No. 15/476,898, Dec. 31, 2018 Non-Final Action.

* cited by examiner

DUAL FREQUENCY ULTRASOUND TRANSDUCER INCLUDING AN ULTRAHIGH FREQUENCY TRANSDUCER STACK AND A LOW FREQUENCY ULTRASOUND TRANSDUCER STACK

CROSS-REFERENCE TO RELATED APPLICATIONS

The present application is a continuation of U.S. patent application Ser. No. 15/476,898 filed Mar. 31, 2017, which is related to and claims the benefit of U.S. Provisional Application No. 62/317,326 filed Apr. 1, 2016, which are herein incorporated by reference in their entirety.

TECHNICAL FIELD

The disclosed technology relates to ultrasound imaging transducers and in particular to dual frequency ultrasound imaging transducers.

BACKGROUND

There are several applications for extremely high bandwidth transducers for imaging using non-linear contrast agents and various forms of signal processing designed to enhance tissue contrast resolution and blood detection for example. However, practical limitations to the achievable bandwidth of transducers limit the applications of these promising imaging techniques. Those skilled in the art will be familiar with the concept of dual frequency transducers. The concept of combining two, or even more, transducers into a single acoustic stack or some geometric combination to allow for the use of two bandwidths in concert in some form has been suggested. However, this is a new concept that has not yet found widespread use or success. One significant limitation currently limiting the utility of dual frequency transducers is the lack of an array-based solution. A second challenge is that of superposition of widely differing center frequency transducers on the same acoustic axis.

SUMMARY

As will be explained in further detail below, the disclosed technology relates to dual frequency ultrasound transducers that can be practically manufactured. In one embodiment, a dual frequency transducer includes a high frequency transducer with a low frequency transducer mounted behind or proximal to the high frequency transducer. In one embodiment, a non-linear ultrasound absorbing material is positioned between a front face of the low frequency transducer and a rear surface of the high frequency transducer. In one embodiment, the ultrasound absorbing material strongly absorbs high frequency ultrasound signals while passing low frequency ultrasound signals. In accordance with some aspects of the disclosed technology, the low frequency transducer is oriented at an angle with respect to the high frequency array such that the low frequency stack is rotated about either the axis normal to the azimuthal plane (roll angle), the axis normal to the elevation plane (pitch angle), or both. The resulting orientation of the low frequency array compared with the orientation of the high frequency transducer is such that a front face of the low frequency transducer is not parallel with a front face of the high frequency transducer.

DESCRIPTION OF THE PREFERRED EMBODIMENTS

In order to realize more of the benefits of a dual frequency transducer, the disclosed technology relates an ultrasound transducer having both high and low frequency elements in the same transducer assembly. In addition, both the low frequency and high frequency transducer elements can be formed as an array to allow beam forming from both the low and high frequency elements. Finally, the low and high frequency elements can have a wide separation of high and low center frequencies of operation to enhance the ultra-wide bandwidth character that is the motivation for making a dual frequency array at all.

In accordance with one embodiment of the technology disclosed herein, a dual frequency transducer design has both low and high frequency array elements that are highly separated in operating frequency, with the HF array having a center frequency (CF) of 15-30 MHz or higher and the LF transducer (which may or may not be a multi-dimensional array array) having a CF of about 1-5 MHz. These two transducers are located generally one behind the other (when viewed along a longitudinal axis of a transducer housing that holds the transducers) such that signals to and from the low frequency transducer pass through the high frequency transducer. In addition both transducers share the same elevation lens.

As will be understood by those skilled in the art, challenges related to a coaxial or nearly coaxial dual frequency array of transducers include the difficulty of eliminating reflections, multipath reverberations, and other artifacts arising from acoustic interactions between the components of the LF transducer array and those of the HF transducer array. One skilled in the art will understand that the LF and HF transducers can be chosen to have sufficiently different bandwidths so as to be largely unaffected by reverberations caused by the each other. However, the problems of in-band reflections and multi-path reverberations arising between components of the two acoustic stacks remain.

Impedance matching the LF transducer elements and kerfs to the backing material of the HF array is one approach that could be undertaken to minimize multi-path reverberations. Such impedance matching is challenging since it is inherently narrow band, and might be different for each material in the stack. If one considers the LF transducer to be an array for example, one skilled in the art will appreciate that impedance matching for the high frequency reverberations will require a different matching solution for the kerfs placed in the LF array compared to the LF transducer elements. Such a solution is highly difficult and impractical. Any impedance mismatch at the face of the LF array will give rise to strong reverberation artifacts in the image created from signals from the HF array.

Two aspects of the technology disclosed herein that can be used alone or in combination, include placing a frequency dependent backing or dampening material that is virtually opaque to HF frequency ultrasound and highly transparent to LF ultrasound (1-5 MHz) between the transducers. In additional or separately, the orientation of the front face of the low frequency transducer can be selected such that it is not parallel to the front face of the HF transducer array to remove multi-path reflection artifacts images produced from signals generated by the HF transducer.

Figure 1:
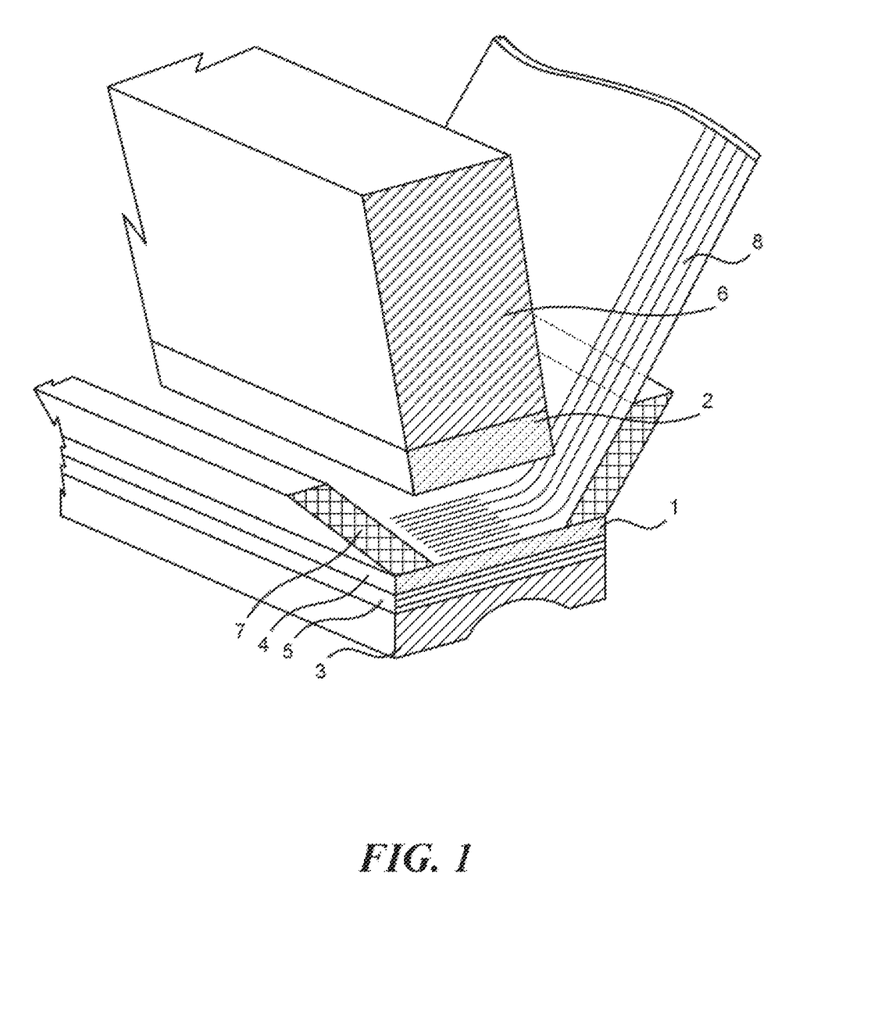
FIG. 1 illustrates an embodiment of the disclosed technology showing a dual frequency ultrasound transducer including a low frequency (LF) ultrasound transducer stack positioned generally behind, or proximal to, a high frequency (HF) ultrasound stack in accordance with some embodiments of the disclosed technology.

As shown in FIG. 1, a dual frequency transducer includes a high frequency transducer stack 1 and a low frequency transducer 2 that is positioned generally behind or proximal to the high frequency transducer stack 1. The high frequency transduced stack 1 generally comprises an array of elements formed into a sheet of HF piezo material 4 that is coupled to a lens 3 through one or more matching layers 5. A support structure 7 (such as a metal frame e.g. molybdenum) supports the high frequency transducer stack 1 as well as one or more flexible printed circuit boards (PCB) e.g. "flex circuits" (8) used to make connection to the HF elements. In one embodiment, the HF array consists of a 30 MHz 256 element HF ultrasound array built in an oversized frame such that the lens 3 is larger than the typical footprint required to accommodate the 30 MHz array. Suitable techniques for making the HF ultrasound array are described in U.S. Patent Publication No. US2014/0350407 A1 and U.S. Pat. No. 8,316,518, which are herein incorporated by reference in their entireties.

A low frequency transducer 2 (e.g. 2 MHz) is positioned behind the HF transducer stack 1. The low frequency transducer 2 electrodes on front and back (not shown) and has a backing material 6 on its rear surface to attenuate low frequency signals travelling in the rearward direction from the low frequency transducer.

Figure 2:
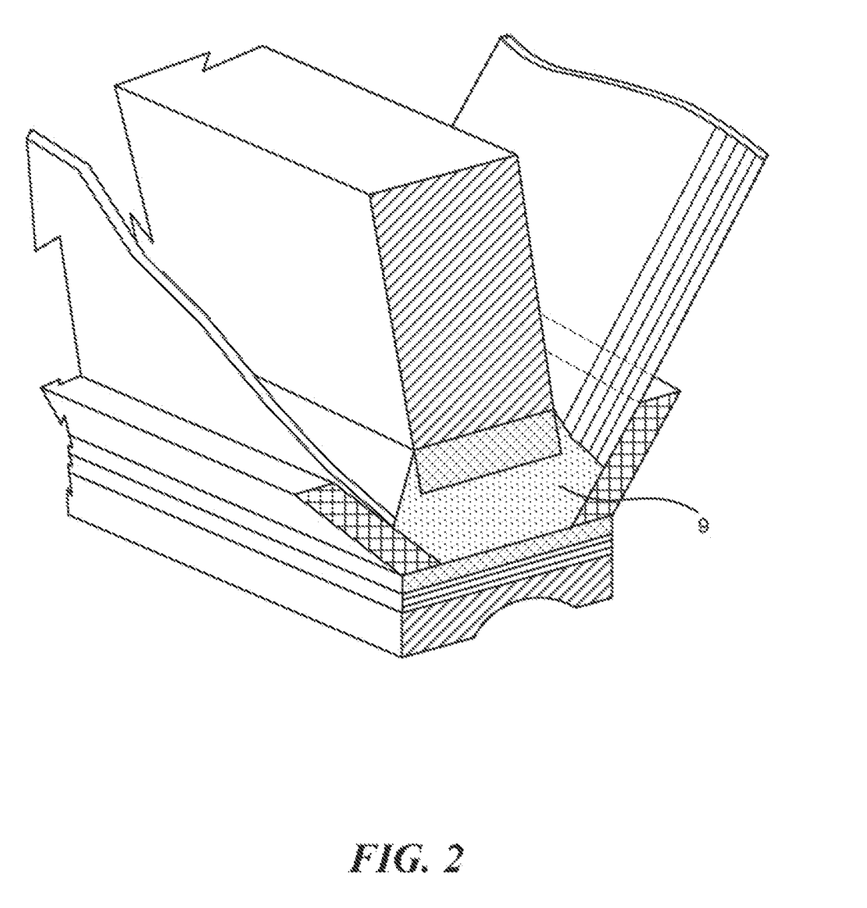
FIG. 2 shows an intermediate acoustic material placed between the low and high frequency stacks in accordance with some embodiments of the disclosed technology.

As shown in FIG. 2, an intermediate dampening material 9 is positioned between a front surface of the low frequency transducer 2 and a rear surface of the 30 MHz HF array. The dampening material 9 is designed to be the acoustic backing of the 30 MHz HF array. The dampening material 9 is selected to exhibit very high losses per unit thickness at 30 MHz, but also to act as the front acoustic coupling medium for the low frequency transducer 2 by exhibiting a relatively low loss/unit thickness at 2 MHz. One skilled in the art will understand that acoustic loss coefficients are typically frequency dependent, and some materials exhibit attenuation that is non-linearly dependent on frequency.

One candidate for such an intermediate dampening material 9 that exhibits a non-linear acoustic attenuation is silicone rubber, which is typically employed as a lens material for ultrasound transducers having center frequencies below 10 MHz. Typical silicone materials exhibit acoustic attenuation in the range of 2-4 dB/cm at 2 MHz, while exhibiting over 10 dB/mm at 30 MHz. This property can be leveraged and enhanced in one embodiment of the disclosed technology by adding small (compared to the 2 MHz wavelength e.g. 2-5 um particle size) and relatively acoustically dissimilar particles to the silicone, causing little change to the low frequency loss, but increasing the loss at 30 MHz to over 25 dB/mm. Suitable choices for the particles include silica powder, silicon dioxide powders, titanium dioxide powders, zirconium dioxide powders or the like, which strongly absorb the high frequency ultrasound signals but due to their size do not act as strong scatterers for the low frequency ultrasound signals. Similarly, other materials besides silicone could be used such as polyurethane, doped epoxies or other materials having highly non-linear loss coefficients versus frequency.

The dampening material 9 enables the placement of the low frequency transducer behind the HF transducer array such that HF ultrasonic waves travelling in the rearward direction from the HF transducer array are attenuated very quickly thereby eliminating any artifact that would arise from internal reflections between the 30 MHz array and the 2 MHz LF transducer. Furthermore, the relatively low attenuation of the powder loaded silicone at 2 MHz allows the low frequency signals to travel out from the 2 MHz low frequency transducer, through the HF piezo sheet 4, and out through the lens 3, making it possible to simultaneously transmit and receive at both high and low frequencies. This embodiment also allows for the use of a composite low frequency transducer or low frequency array with kerfs to be successfully employed, due to the high loss character of the dampening material at 30 MHz. One skilled in the art will understand that if the dampening material was not sufficiently attenuative at high frequency, it would be necessary to attempt to use some form of impedance matching device to ensure that acoustic energy emitted from the HF array and travelling back into the device did not reflect from components of the low frequency transducer and return to the HF array with sufficient energy to give rise to unwanted imaging artifacts.

One skilled in the art will also understand that employing impedance matching to an array with kerfs designed to work efficiently at the LF range or a composite material with such kerfs would present an impractical challenge for the designer and manufacturer, since the LF pitch and kerf dimensions will appear as discrete specular reflectors to the HF energy necessitating a matching system of equal spatial complexity.

As one skilled in the art will understand, the thickness of the dampening material 9 positioned between the high frequency array and the low frequency transducer can be optimized to balance the need for the suppression of multi-path reverberations arising from the HF array with the need for efficient transmission of the LF acoustic energy to the front of the lens. If the layer of dampening material 9 is too thin, then not enough attenuation of the signals from the high frequency transducer will occur. On the other hand, if the layer of dampening material 9 is too thick, then unnecessary losses will occur in the low frequency ultrasound signals and low frequency reverberation could become problematic if it were to persist in time due to an excessively long travel time.

One embodiment of the disclosed technology can have an intermediate dampening material layer 9 made from KE1300T silicone made by Shin Etsu doped with 2-3 um alumina particles to make a material having attenuation coefficients of about 31 dB/mm at 30 MHz and about 2 dB/cm at 2 MHz. An embodiment of the disclosed technology can utilize a layer of this doped silicone having a thickness of about 2.0 mm to achieve a total two way path loss of over 124 dB for the high frequency acoustic wave travelling into the backing and back to the HF array, while having only about 0.3 dB total one way loss for the LF acoustic energy travelling out of the low frequency transducer 2 toward the lens 3.

In one embodiment, a jig or other tool (not shown) is used to hold the low frequency single element transducer or array transducer at a desired distance away from the high frequency array while the space between the two transducers is filled with the dampening material 9 which is allowed to cure thus fixing the LF transducer in place.

Other intermediate dampening material properties can be achieved and combined with other thicknesses to achieve desirable properties for other dual frequency combinations. For example, a 4 MHz low frequency transducer can be combined with a 20 MHz high frequency array and spaced by 3.0 mm using GE RTV60 (a commercial loaded silicone) for the intermediate dampening material. GE RTV60 exhibits loss of about 17 dB/mm at 20 MHz and about 3 dB/cm at 4 MHz. This material will result in a two way path loss of about 102 dB for the 20 MHz acoustic energy, and about 0.9 dB loss for the 4 MHz energy. As one experienced in the art will understand, each combination will exhibit different losses at the respective high and low frequencies being used in the dual frequency design. It will further be understood that obtaining acceptable loss values will be more difficult as the two frequencies are chosen closer together since the attenuation coefficient of the coupling medium is a function of frequency.

In another embodiment of the disclosed technology, the low frequency transducer is a 1 D, a 1.5D, or a 2D array. The elements of the LF array are connected to conductors (not shown) that apply signals to and receive signals from the array elements. Because the LF array elements are so much larger than those of the HF array, it is not difficult to route conductors to each of the array elements even if they are arranged in more than a single dimension and since the LF array is sized to correspond to the HF array.

Figure 3:
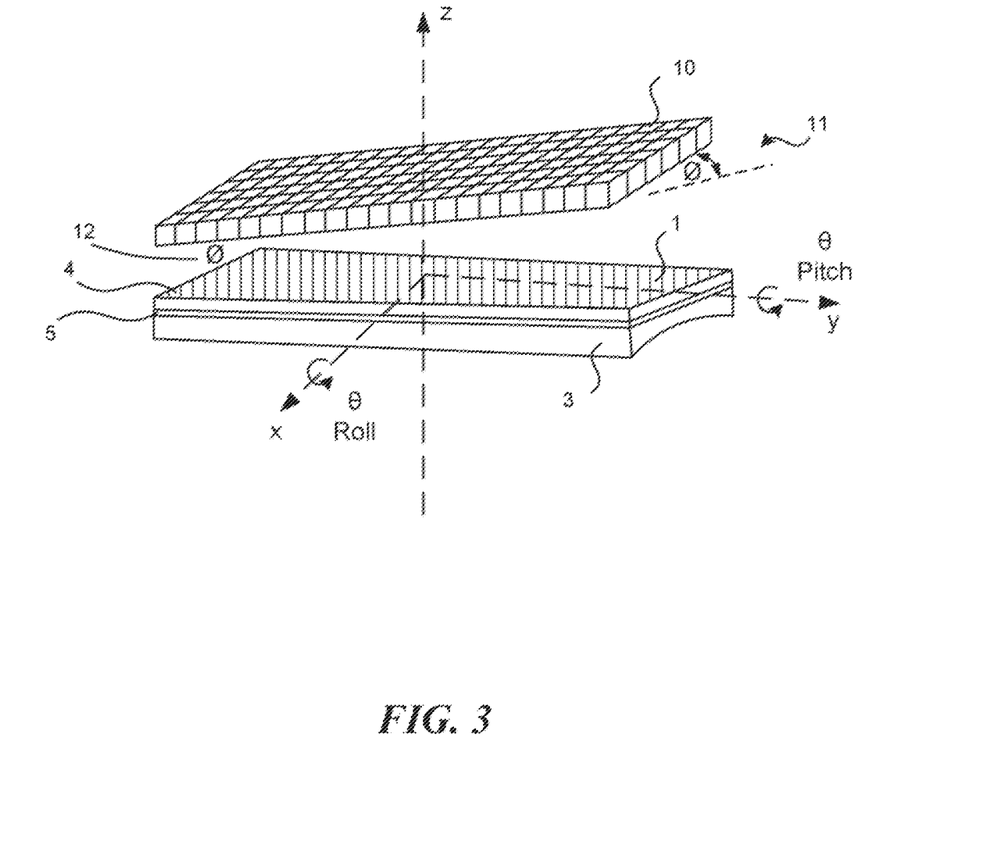
FIG. 3 depicts a low frequency ultrasound transducer stack that is oriented with one or more of an azimuthal (or roll) and an elevation (or pitch) angle that is offset with respect to an acoustic axis of the HF transducer stack in accordance with some embodiments of the disclosed technology.
Figure 4:
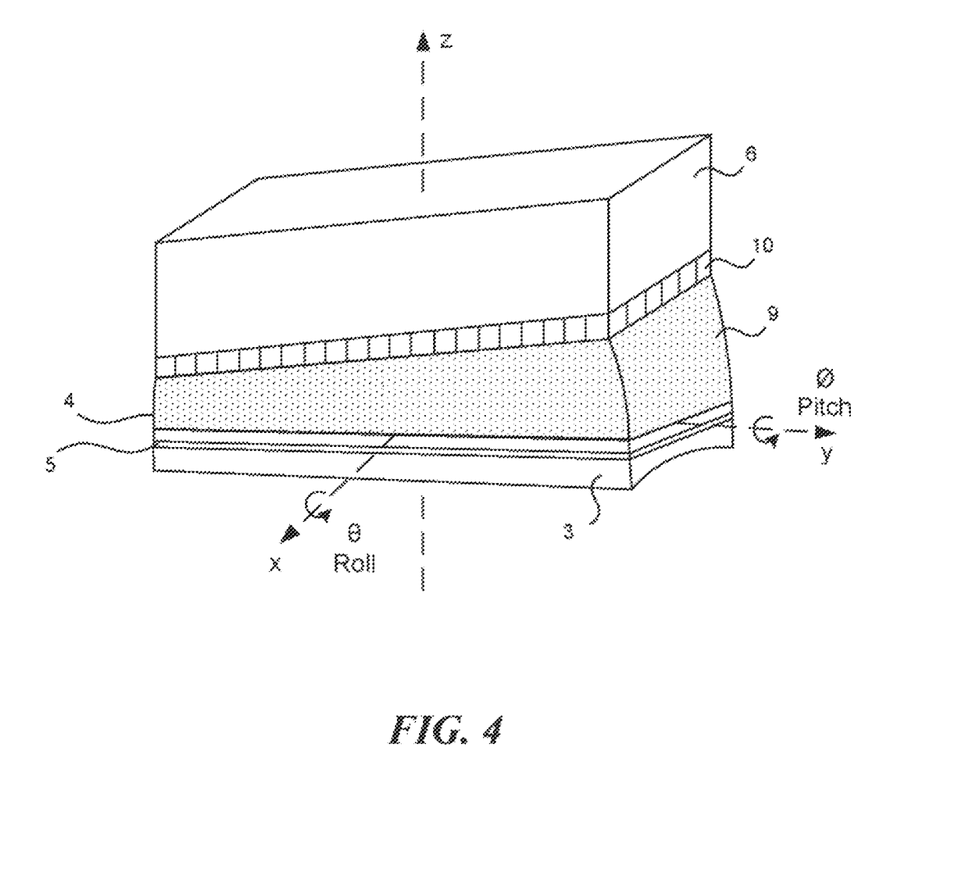
FIG. 4 depicts a low frequency ultrasound transducer stack and a backing material coupled to the high frequency ultrasound stack with the intermediate acoustic material in place in accordance with some embodiments of the disclosed technology.

In some embodiments of the disclosed technology, the low frequency array is rotated about one or both of its elevation (shown as pitch in FIG. 3) and azimuthal (shown as roll in FIG. 3) axes compared with the axes of the high frequency transducer. One skilled in the art will appreciate that either of these two rotations alone will act to mitigate multipath reflections between the high and low frequency transducers and their components. Together, the two rotations greatly mitigate such multipath reflections. However, such rotations also make coaxial operation of the low and high frequency arrays impossible using normal (perpendicular to the face of the LF stack) beam forming. However, one aspect of the technology disclosed herein will be recognized to overcome this limitation.

In some embodiments of the disclosed technology, the low frequency array is a 1.0D, 1.5D or 2D array that is driven by beamforming hardware and/or software with a delay profile configured to direct the beams produced by the low frequency array in a direction that compensates for the fixed rotational offsets of the LF transducer, thereby allowing the LF array transducer to produce a normal acoustic signal that is coaxial with the signals produced by the high frequency array. As will be understood by those or ordinary skill in the art, beamforming may be done in a processor, DSP or ASIC or other logic by selectively varying one or more of the weights and delays applied to the signals transmitted/received by the arrayed transducer elements to change the effective beam direction. For example, if the transducer is only rotated in the azimuthal direction compared to the forward looking direction of the HF array, then driving signals produced for LF transducer elements can be driven with an element delay profile that can steer the beam to compensate for the physical rotation of the LF transducer. On the receive side, similar delays/weights are employed for the signals produced by the transducer elements to reconstruct the incoming coaxial beam to compensate for the rotation of the LF transducer with respect to the plane of the HF transducer If a 1.5D or 2D array is used, then similar software or hardware delays are used for the driving and receive signals to compensate for the rotational offsets of the LF array with respect to the plane of the HF transducer array.

One skilled in the art will appreciate that such an offset in the orientation of the low frequency array with respect to the high frequency array will further mitigate any multipath reflection, allowing the designer to choose the intermediate backing/front coupling material to have a very low loss at low frequency, since it becomes less critical to reduce the high frequency attenuation due to the angled low frequency array orientation. In addition, low frequency inter-stack reverberations will be virtually eliminated with the use of one or more of the azimuthal (roll) and elevation (pitch) offset angles, allowing the designer to optimize the inter-stack distances and materials based on parameters other than simply the minimization of multipath reverberations.

One skilled in the art will understand that the designer can trade off the HF and LF frequency separation, distance between the HF and LF arrays, rotational offset angles, and the attenuation properties of the intermediate dampening material in order to maximize the properties of the dual frequency array to suit the application. For example, a designer could select a high acoustic impedance intermediate damping material such as epoxy doped with heavy particles such as tantalum oxide, hafnium oxide or some other heavy non-conductive particles for example, to improve acoustic bandwidth of the high frequency array. One skilled in the art will understand that a loaded epoxy layer will have much lower acoustic loss at high frequency than, for example, a silicone based layer, giving rise to perhaps unacceptably high multi-path reverberation artifacts. In this case, the designer can employ another aspect of the of the disclosed technology, specifically the rotational offset angles in for example both elevation and azimuthal directions. The designer can then according to the disclosed technology, employ a 2D array with fixed beam steering and having sufficiently small pitch and directivity properties to provide sufficient steering performance to cancel the offset angles thus achieving a coaxial dual frequency array having highly mitigated multi path reverberations. Again, one skilled in the art will understand that such a 2D array could further be driven with suitable delay profiles combined with the fixed offset profiles to achieve a standard beam focusing and scanning as required with respect to the underlying beam trajectory.

It is further possible for the LF array to be driven with a wide range of beam forming techniques in both transmit and receive while applying the required fixed correction delay profiles to compensate for any pitch and/or roll offsets employed in the design of the DF probe. It will be further understood that correction for fixed pitch and roll offset need not be perfect to provide substantially the same benefits of fully coaxial operation. This invention may be employed to partially correct for pitch and/or roll offsets such that the resulting LF beam has an angular offset from the HF beam, however, as will be understood by those skilled in the art, the LF beam width will generally be larger than the HF beam width by a factor proportional to the high frequency divided by the low frequency. For example, a 2 MHz/30 MHz dual frequency array will have a low frequency beam on the order of 30/2=15 times wider than the 30 MHz beam. As such, small angular differences between the axis of the LF and HF arrays are of little consequence up to perhaps as much as 5 degrees for example. It should be understood that correction for rotational offset angles need not be complete and in fact can be intentionally incomplete, employed as an engineering trade-off to allow, for example, the designer to simplify the design of the LF array (i.e. having larger pitch in a 2D array thus allowing less steering correction) while still offsetting the LF stack sufficiently to eliminate multipath reflections in the HF stack.

Figure 5:
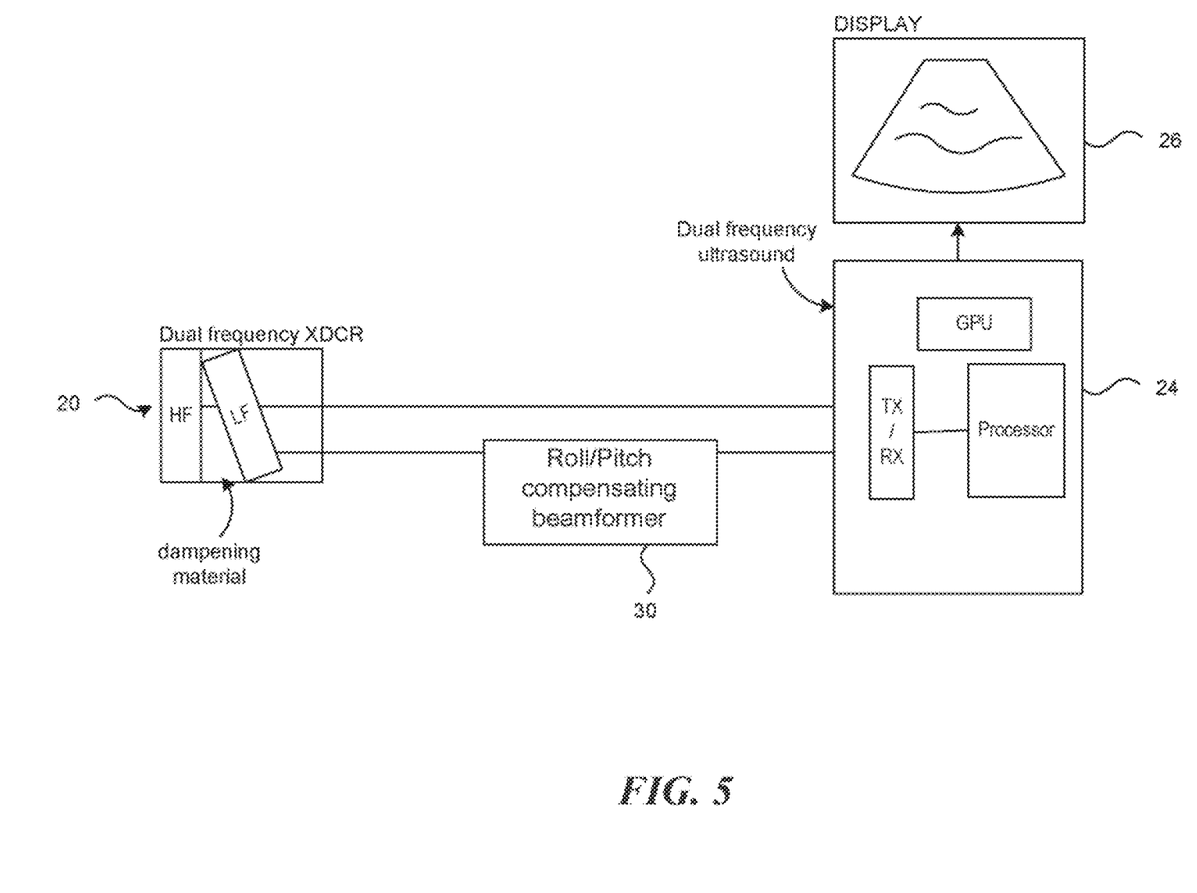
FIG. 5 illustrates a block diagram of a dual frequency ultrasound system including a dual frequency probe and a beamformer that compensates for one or more of a roll or pitch offset of a low frequency transducer in accordance with an embodiment of the disclosed technology.

FIG. 5 is a block diagram of a dual frequency ultrasound system in accordance with one embodiment of the disclosed technology. The system includes a dual frequency transducer 20 having both a high frequency (HF) transducer and low frequency transducer including means for reducing inter-stack multipath reflections by one or more of a dampening material that exhibits high absorption of HF ultrasound signals while passing LF ultrasound signals and an offset in a roll axis, pitch axis or both of the front face of the LF transducer with respect to the HF transducer. Driving signals for the dual frequency transducer are provided by a dual frequency ultrasound machine 24 including conventional components such as transmit/receive circuitry, one or more processors, graphics processing units and memory, communication circuitry etc. A display 26 produces visual images of ultrasound signals captured using both the HF and LF transducer.

A compensating beamformer 30 is provided to compensate for any offset in the roll and/or pitch of the LF transducer. Because the physical orientation of the LF transducer is fixed with respect to the HF transducer, the beamformer can employ fixed delays to steer the transmit and receive beams in a direction that is co-axial or nearly co-axial with the beam produced by the HF transducer. The beamformer 30 can be implemented in a number of ways including a digital signal processor (DSP), an application specific integrated circuit (ASIC), an FPGA employing fixed delays and sum operations in the transmit or receive paths, a programmable processor implementing and the like. The beamformer 30 operates in addition to beamforming provided by the ultrasound machine 24 to steer the beams over a sweep angle. It should be noted that it is possible for the ultrasound machine to perform the compensation for offset as part of the LF image beamforming rather than relying on a separate compensating beamformer, and that such an arrangement is not outside the scope of this invention.

From the foregoing, it will be appreciated that specific embodiments of the disclosed technology have been described herein for purposes of illustration, but that various modifications may be made without deviating from the scope of the disclosed technology. For example although the disclosed embodiments are describes as a 30 MHz HF transducer and a 2 MHz LF transducer, it will be appreciated that the center frequencies of the transducers could be changed. Accordingly, the disclosed technology is not limited except as by the appended claims. In addition, one skilled in the art will understand that many configurations of LF array and offset angles could be devised in light of the aspects of this invention to produce numerous configurations of coaxial and nearly coaxial dual frequency array based probes.

We claim:

1. A dual frequency ultrasound system, comprising:
a dual frequency ultrasound transducer including:
a low frequency (LF) ultrasound transducer positioned behind a high frequency (HF) ultrasound transducer, and
a dampening layer disposed between a front face of the LF ultrasound transducer and a rear face of the HF ultrasound transducer for reducing inter-stack multipath reflections, wherein
the dampening layer has attenuation properties that increase non-linearly with increasing frequency, and
the dampening layer exhibits acoustic attenuation of about 2-4 dB/cm at about 2 MHz, and the dampening layer exhibits acoustic attenuation of at least 10 dB/mm at about 30 MHz;
a dual frequency ultrasound machine coupled to the dual frequency ultrasound transducer to provide driving signals to the dual frequency ultrasound transducer; and
a display coupled to the dual frequency ultrasound machine to provide visual images of ultrasound signals captured using the dual frequency ultrasound transducer.

2. The dual frequency ultrasound system of claim 1, wherein the LF transducer is an arrayed transducer.

3. The dual frequency ultrasound system of claim 2, wherein the LF transducer is one of a 1D, 1.5D, and 2D array.

4. The dual frequency ultrasound system of claim 1, wherein the HF transducer is an arrayed transducer.

5. The dual frequency ultrasound system 1 of claim 1, wherein the dampening layer comprises an elastomer.

6. The dual frequency ultrasound system of claim 5, wherein the elastomer is silicone.

7. The dual frequency ultrasound system of claim 5, wherein the elastomer is doped with a powder that acts as scatterers for signals produced by the HF ultrasound transducer but do not substantially affect the signals produced by the LF ultrasound transducer.

8. The dual frequency ultrasound system of claim 1, wherein a first axis normal to a front face of the HF transducer is parallel with a second axis normal to a front face of the LF transducer such that the LF and HF ultrasound transducer beams share a common acoustic axis.

9. A dual frequency ultrasound system, comprising:
a dual frequency ultrasound transducer including a low frequency (LF) ultrasound transducer positioned behind a high frequency (HF) ultrasound transducer such that the LF ultrasound transducer is rotated in one or more of a roll and pitch such that a first axis normal to a front face of the HF transducer is not parallel with a second axis normal to a front face of the LF transducer, wherein
the dual frequency ultrasound transducer further comprises a dampening layer disposed between a front face of the LF ultrasound transducer and a rear face of the HF ultrasound transducer for reducing inter-stack multipath reflections,
the dampening layer has attenuation properties that increase non-linearly with increasing frequency, and
the dampening layer exhibits acoustic attenuation of about 2-4 dB/cm at about 2 MHz, and the dampening layer exhibits acoustic attenuation of at least 10 dB/mm at about 30 MHz;
a beam former configured to adjust a direction of transmit and receive beams of the LF ultrasound transducer such that the LF and HF ultrasound transducer beams both share a common acoustic axis;

a dual frequency ultrasound machine coupled to the dual frequency ultrasound transducer to provide driving signals to the dual frequency ultrasound transducer; and a display coupled to the dual frequency ultrasound machine to provide visual images of ultrasound signals captured using the dual frequency ultrasound transducer.

10. The dual frequency ultrasound system of claim 9, wherein the LF transducer is an arrayed transducer.

11. The dual frequency ultrasound system of claim 10, wherein the LF transducer is one of a 1D, 1.5D, and 2D array.

12. The dual frequency ultrasound system of claim 9, wherein the HF transducer is an arrayed transducer.

13. The dual frequency ultrasound system of claim 9, wherein the dampening layer comprises an elastomer.

14. The dual frequency ultrasound system of claim 13, wherein the elastomer is silicone.

15. The dual frequency ultrasound system of claim 13, wherein the elastomer is doped with a powder that acts as scatterers for signals produced by the HF ultrasound transducer but do not substantially affect the signals produced by the LF ultrasound transducer.

\* \* \* \* \*